United States Patent
Takahashi

(10) Patent No.: US 8,075,479 B2
(45) Date of Patent: Dec. 13, 2011

(54) ENDOSCOPE

(75) Inventor: Masaya Takahashi, Hachioji (JP)

(73) Assignee: Olympus Corporation, Tokyo (JP)

( * ) Notice: Subject to any disclaimer, the term of this patent is extended or adjusted under 35 U.S.C. 154(b) by 1124 days.

(21) Appl. No.: 11/827,345

(22) Filed: Jul. 11, 2007

(65) Prior Publication Data

US 2008/0021279 A1 Jan. 24, 2008

(30) Foreign Application Priority Data

Jul. 19, 2006 (JP) ................... 2006-196441

(51) Int. Cl.
*A61B 1/06* (2006.01)
(52) U.S. Cl. ................................. 600/167
(58) Field of Classification Search ............. 600/103, 600/129, 143, 167–168, 173
See application file for complete search history.

(56) References Cited

U.S. PATENT DOCUMENTS

| | | | | |
|---|---|---|---|---|
| 4,777,524 A * | 10/1988 | Nakajima et al. | ............. | 348/76 |
| 5,231,473 A * | 7/1993 | Kawamura et al. | ........... | 359/694 |
| 5,531,664 A * | 7/1996 | Adachi et al. | ................ | 600/149 |
| 6,117,071 A * | 9/2000 | Ito et al. | ........................ | 600/168 |
| 6,185,375 B1 * | 2/2001 | Mikami | .......................... | 396/84 |
| 6,409,658 B1 * | 6/2002 | Mitsumori | .................... | 600/167 |
| 6,413,207 B1 * | 7/2002 | Minami | ........................ | 600/109 |
| 6,447,447 B1 * | 9/2002 | Mitsumori | .................... | 600/167 |
| 7,294,102 B2 * | 11/2007 | Jones et al. | .................. | 600/151 |
| 7,338,439 B2 * | 3/2008 | Kanai | ........................... | 600/176 |
| 2002/0016526 A1 * | 2/2002 | Akiba | .......................... | 600/167 |
| 2004/0097791 A1 * | 5/2004 | Tokuda et al. | ............... | 600/173 |
| 2008/0227060 A1 * | 9/2008 | Esashi et al. | ................. | 434/113 |

FOREIGN PATENT DOCUMENTS

| | | |
|---|---|---|
| JP | 05-038326 | 2/1993 |
| JP | 10-307628 | 11/1998 |
| JP | 11-169336 | 6/1999 |
| JP | 2004-129950 | 4/2004 |

* cited by examiner

*Primary Examiner* — Philip Smith
(74) *Attorney, Agent, or Firm* — Scully, Scott, Murphy & Presser, P.C.

(57) ABSTRACT

In a drive mechanism which displaces a movable lens to be displaced, a shape memory element which is displaced due to heating. A displaceable range of a movable lens is restricted between a first position and a second position. With the shape memory element in a heated state upon applying a predetermined amount of heat to the shape memory element, the movable lens is displaced to the first position, and when the shape memory element is not heated, the movable lens is displaced to the second position. During a normal observation, a time for which the movable lens is displaced to the second position is longer than a time for which the movable lens is displaced to the first position.

4 Claims, 4 Drawing Sheets

ENDOSCOPE

CROSS-REFERENCE TO RELATED APPLICATION

The present application is based upon and claims the benefit of priority from the prior Japanese Patent Application No. 2006-196441 filed on Jul. 19, 2006; the entire contents of which are incorporated herein by reference.

BACKGROUND OF THE INVENTION

1. Field of the Invention

The present invention relates to an endoscope.

2. Description of the Related Art

In an endoscope which includes an image pick-up unit at a front end portion, and which is provided with a flexible tube having a bent portion, generally, for observing an endoscope image in an optimum state, it is necessary to adjust a focal point by moving a focusing lens and an image pick-up element.

As an endoscope apparatus for solving this problem, an image pick-up apparatus for endoscope described in Japanese Patent Application Laid-open Publication No. 2004-129950 has been proposed. In the image pick-up apparatus for endoscope according to this proposal, at a front end portion of the endoscope, a shape memory alloy is let to be a variable means of relative positions of an optical element and an image pick-up element.

However, when a shape memory element is used in an actuator which drives a lens as in a conventional technology, generally, when the shape memory alloy is held for a long time with a load exerted thereon, in a heated state, a lattice defect is developed inside, and a function as an actuator is declined.

Since this developing becomes remarkable when a shape memory treatment having a substantial displacement due to heating is carried out, there is a problem that it has been difficult to achieve a substantial displacement for using stably for a long period of time.

Moreover, for restricting a movable range of a lens accurately, it is desirable to restrain mechanically the movable range of the lens. However, in such structure in which a movement margin is taken into consideration, a substantial stress is exerted on a shape memory alloy at the time of heating. Therefore, the abovementioned problem is particularly remarkable.

SUMMARY OF THE INVENTION

The present invention is made in view of these points, and an object of the present invention is to provide an endoscope in which a stable range operation is possible over a long period of time while achieving a comparatively substantial displacement of the lens, by optimizing a structure with respect to a state frequency of an actuator in an actual working condition.

To solve the abovementioned problems, and to achieve the object, according to the present invention, it is possible to provide an endoscope which includes a front end portion, at which an image pick-up unit which has an optical system which changes an image-formation range by focusing by displacing at least a part of a lens group, is disposed.

In a driving mechanism which displaces the range group to be displaced, a shape memory element which is displaced by heating is let to be a driving force, and a displaceable range of the lens group is restricted between a first position and a second position.

With the shape memory element in a heated state by imparting a predetermined amount of heat to the shape memory element, the lens group to be displaced is displaced to the first position, and when the shape memory element is not heated, the lens group to be displaced is displaced to the second position.

During a normal observation, a time for which the position of the lens group to be displaced is displaced to the second position is longer than a time for which the position of the lens group to be displaced is displaced to the first position.

Moreover, according to a preferable aspect of the present invention, it is desirable that an image-formation range of focusing when a position of the lens group to be displaced is the second position is wider than an image-formation range of focusing when the position of the lens group to be displaced is the first position.

Furthermore, according to a preferable aspect of the present invention, it is desirable that the position of the lens group to be displaced is restricted by constraining mechanically between the first position and the second position.

According to a preferable aspect of the present invention, it is desirable that a bias spring which exerts a force on the lens group to be displaced, toward the second position is fitted into the drive mechanism which displaces the lens group to be displaced.

According to a preferable aspect of the present invention, it is desirable that the endoscope includes a bending tube which can be bent, and which is connected to the front end portion, and the shape memory element is interpolated into a tube member which can be bent, and the shape memory element and the tube member are extended to the bending portion, and the tube member and the shape memory element are coupled at an end portion of the tube member, toward the bending tube, and the other end of the tube member is fixed to a predetermined part of the front end portion, and the other end of the shape memory element is fixed to the lens group to be displaced.

DETAILED DESCRIPTION OF THE INVENTION

An embodiment of an endoscope according to the present invention will be described below by referring to the accompanying diagrams. However, the present invention is not restricted to this embodiment.

Figure 1:
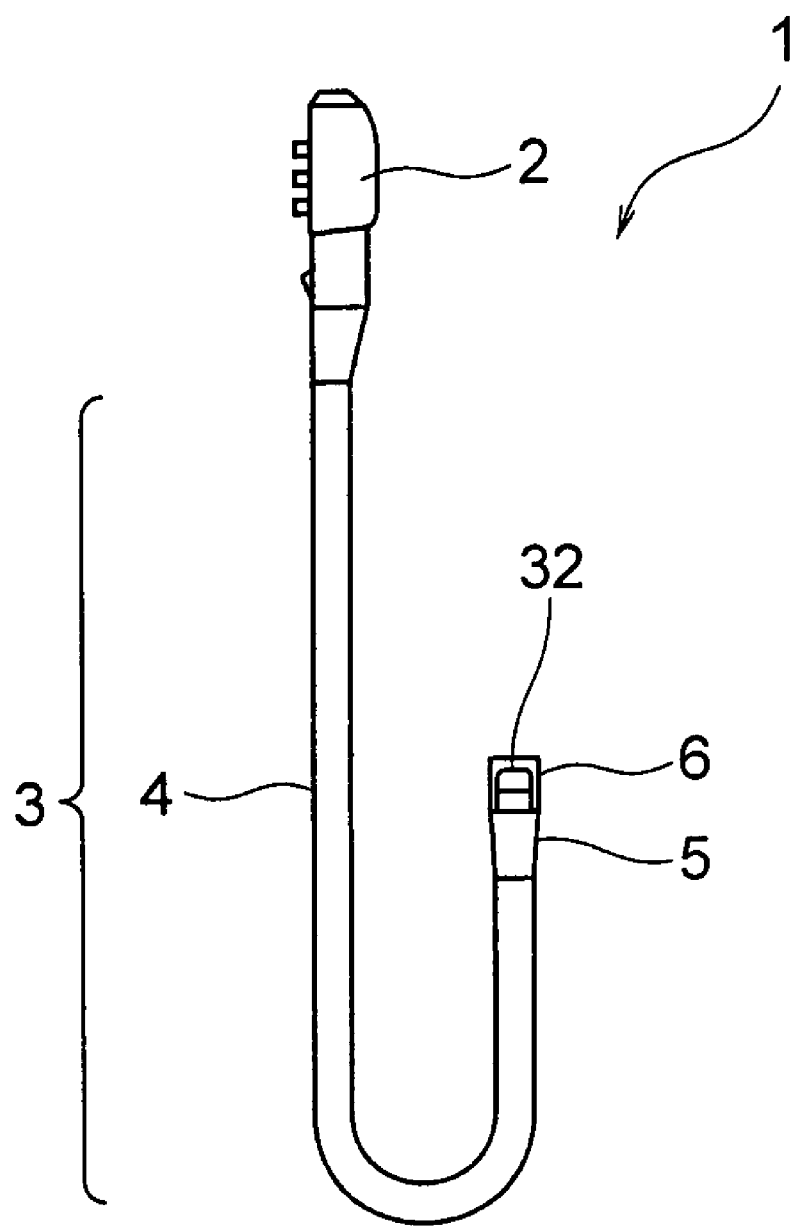
FIG. 1 is a diagram showing a schematic structure of an entire endoscope apparatus according to an embodiment of the present invention.

FIG. 1 shows a schematic structure of an endoscope 1. As shown in FIG. 1, the endoscope 1 includes an operating section 2 which performs a bending operation, and a control of a pipe conduit system, an inserting section 3 which is inserted into a body cavity of an object to be examined, and a rear-end side of which is connected to the operating section 2.

The inserting section 3 includes a flexible tube 4 having a bending section 5 which can be bend and which is provided at a front end side of the flexible tube 4, and a front end section 6 which is hard and which is provided at a front end side of the bending section 5. An image pick-up element unit 32 which picks up an image of a part to be observed inside the body cavity, and which will be described later is built-in in the front end section 6.

Figure 2:
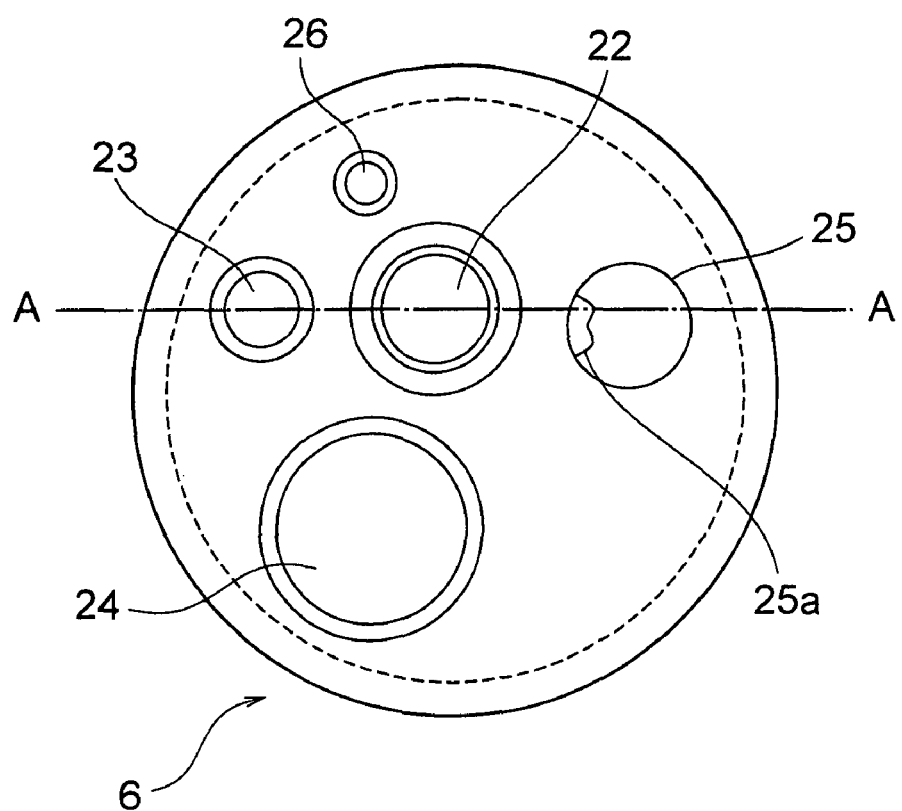
FIG. 2 is a diagram showing a front-view of the endoscope apparatus according to the embodiment.

FIG. 2 shows a front view of a front end portion to be inserted of the endoscope in FIG. 1. As shown in FIG. 2, in a front-end surface 21 of the front end section 6, an observation window 22, an illumination window 23, an endoscopic instrument inserting channel aperture section 24, a gas-water supply nozzle 25, and a front water supply channel aperture section 26 are disposed. The observation window 22 functions as a lens which forms the image pick-up unit 32 which will be described later. The illumination window 23 functions as a lens which forms each of light guide units, the endoscopic instrument inserting channel aperture section 24 is an aperture section of a channel for inserting an endoscopic instrument. The gas-water supply nozzle 25 is an aperture section of a gas-water supply channel 25a which is for washing the observation window 22. The front water supply channel aperture section 26 is an aperture section of front water supply channel for washing a liquid such as mucus and blood of a patient subjected to examination.

Figure 3:
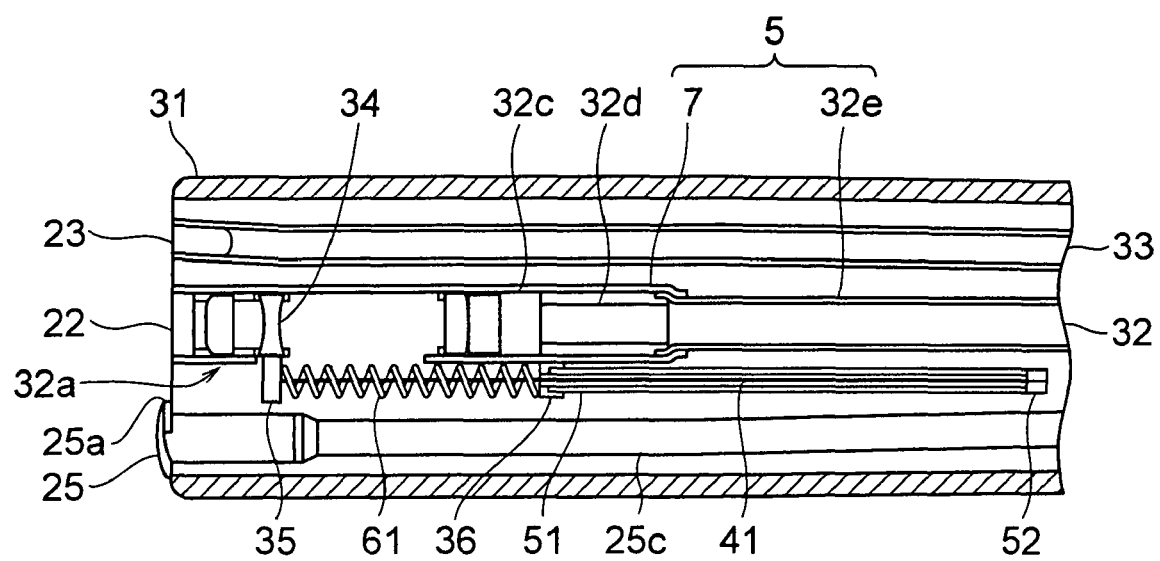
FIG. 3 is a diagram showing a cross-sectional view of the endoscope apparatus according to the embodiment.
Figure 4:
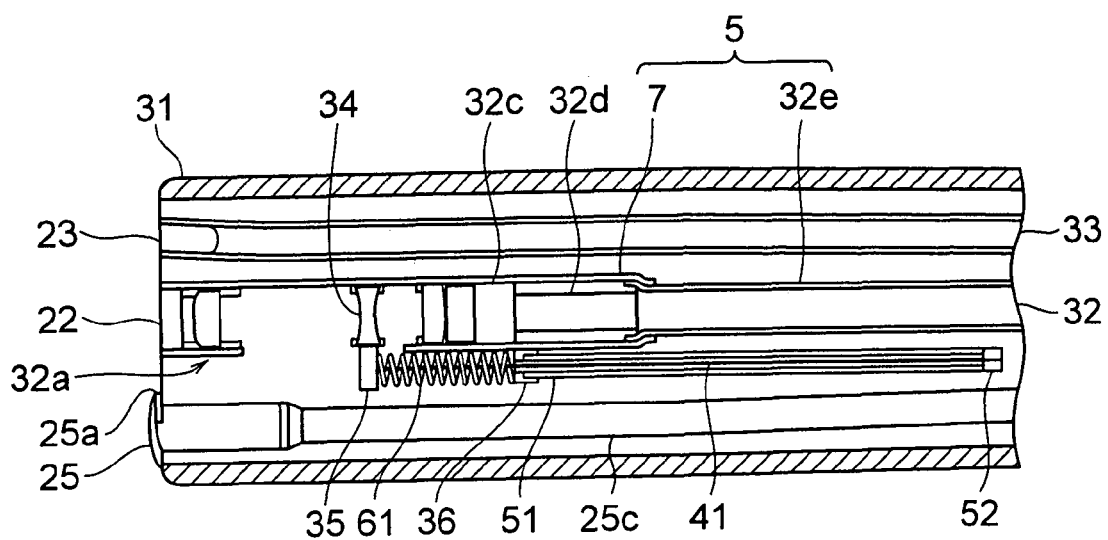
FIG. 4 is a diagram showing a cross-sectional view of the endoscope apparatus according to the embodiment.

FIG. 3 and FIG. 4 show a cross-sectional view of a front end section along a line A-A in FIG. 2. As shown in FIG. 4, the front end section 6 is provided with a hard front end section body which is not described. Built-in components such as the image pick-up unit 32 corresponding to the observation window 22 and a light guide unit 33 corresponding to the illumination window 23 are disposed in the front end section main body. Moreover, the front end section main body is covered by a front end cover 31.

The image pick-up unit 32 includes the observation window 22, an objective optical system 32a, an image pick-up element 32c, and a circuit substrate 32d, and is held by a lens barrel 7. The objective optical system 32a is provided at a rear end side of the observation window 22, and is formed by a plurality of lens groups. The image pick-up element 32c which is a solid image pick-up element such as a CCD (charge coupled device) is disposed at a rear end side of the objective optical system 32a. The circuit substrate 32 to which, the image pick-up element 32c is connected carries out various processes such as signal amplification.

A signal cable 32e which is extended from the circuit substrate 32d is inserted through the inserting section 3, in the image pick-up unit 32. The objective optical system 32a includes a movable lens 34. The movable lens 34 is supported by a movable lens frame 35.

One end of a shape memory element 41 which is in the form of a wire is fixed to the movable lens frame 35, and the shape memory element 41 is accommodated in a tube 51 which can be bent, and which is fixed to a tube fixing member 36 of the lens barrel 7.

The structure is such that the tube 51 which accommodates the shape memory element 41 is inserted through the bending section 5 which is formed to be tapered shaped such that a side from inside of the front end section 6 up to a side of the front end section 6 is thick, inside the flexible tube 4, one end of the tube 51 is clamped to one end of the shape memory element 41 by a caulking for fixing 52, and one end of the shape memory element 41 is fixed.

The shape memory element 41 has a property of getting displaced, or getting contracted in particular when heated up to a transformation temperature, and getting slackened when cooled down to the transformation temperature. A shape memory element in the form of a wire which expands and contracts according to the temperature is to be used. One end of a coiled spring for bias 61 is fixed to the tube fixing member 36. The other end of the coiled spring for bias 61 is fixed to the movable lens frame 35.

The movable lens frame 35 is in a state of being pushed by a stress of the coiled spring for bias 61. When the shape memory element 41 is not deformed by the stress of the coiled spring for bias 61, the movable lens 34 is in a state of being held at a fixed position. When the movable lens 34 is in the state of the position held by the stress of the coiled spring for bias 61, without being affected by a force from the shape memory element 41, the objective optical system 32a is set such that an image-formation range formed by the objective optical system 32a becomes wide.

Since the position of the movable lens 34 is held by the stress of the coiled spring for bias 61, the movable lens 34 is held at a fixed position at each movement, without being affected by the shape memory element 41. Therefore, the image-formation range formed by the objective optical system 32a becomes constant. Moreover, since the shape memory element 41 has a structure extended up to the inside of the bending section 4, it is possible to achieve a substantial amount of displacement of the movable lens 34.

FIG. 4 shows a state when the movable lens 34 is driven by deforming the shape memory element 41 from a state shown in FIG. 3. By a power supply which is not shown in the diagram, an electric voltage is applied to both ends of the shape memory element 41, and the shape memory element 41 is heated up to a temperature beyond the transformation temperature. By heating the shape memory element 41 beyond the transformation temperature, the shape memory element 41 is contracted.

Since a contraction generating force is larger than the stress of the coiled spring for bias 61, when the shape memory element becomes shorter than a distance between one end fixed to the one end of the tube 51, and a connecting point with the movable lens frame 35, the movable lens 34 moves. An amount of contraction of the shape memory element 41 is determined by a length of the shape memory element 41, and according to the amount of contraction of the shape memory element 41, the movable lens 34 assumes a state of being held at a fixed position.

Moreover, a member which stops the movable lens 34 upon being struck when the shape memory element 41 is contracted may be disposed in a movable area of the movable lens 34 (an area in which the movable lens 34 moves), and the movable lens 34 may be held at a fixed position by constraining mechanically. It is particularly preferable, since in this case, it is possible to let the position of the movable lens 34 fixed at the time of heating irrespective of unevenness in the amount of contraction of the shape memory alloy 41, and bending of the endoscope.

When the movable lens 34 is in the state of being held by a contraction force of the shape memory alloy 41, the image-formation range formed by the objective optical system 32a is narrow as compared to the image-formation range in FIG. 3, and the objective optical system 32a is set such that an observation of an image which is enlarged further, is possible. The state in FIG. 3 corresponds to a second position. The state in FIG. 4 corresponds to a first position.

As a usage of an endoscope which is capable of changing the image-formation range, an object to be examined is observed in a state of wide field of view, and when a part which is suspected of having a pathologic change is found, an enlarged observation of the narrow field of view is assumed to be carried out temporarily.

Moreover, since a state in which the observation of the wide field of view is possible at the time of inserting or taking out the endoscope from an object to be examined is desirable, in a normal usage, it is common that the time of carrying out the observation of the wide field of view is quite longer than the time of carrying out the enlarged observation of the narrow field of view.

Therefore, since the image-formation range of an image formed by the objective optical system 32a when the shape memory element 41 is not heated is wider than the image-formation range of an image formed by the objective optical system 32a when the shape memory element 41 is in a heated state, in the usage of the endoscope, a frequency of the state in which the shape memory element 41 is not heated becomes very high as compared to a frequency of the heated state of the shape memory element 41. Therefore, since a life of the shape memory element 41 becomes long by shortening of a time for which the stress is exerted on the shape memory element 41 upon being heated, it is possible to have a stable operation over a long period of time.

In this manner, the endoscope according to the present invention is useful as an endoscope which displaces the lens.

According to the present invention, an effect is shown that by optimizing a structure with respect to for a frequency of a state of an actuator in an actual state of use, it is possible to provide an endoscope in which a stable range operation is possible over a long period of time while obtaining a comparatively substantial displacement of the lens.

What is claimed is:

1. An endoscope comprising:
   a front end portion at which an image pick-up unit which has an optical system which changes an image-formation range by focusing by displacing at least a part of a lens group, is disposed, wherein
   in a driving mechanism which displaces the range group to be displaced, a shape memory element which is displaced by heating is let to be a driving force, and a displaceable range of the lens group is restricted between a first position and a second position, and
   with the shape memory element in a heated state by imparting a predetermined amount of heat to the shape memory element, the lens group to be displaced is displaced to the first position, and when the shape memory element is not heated, the lens group to be displaced is displaced to the second position,
   during a normal observation, a time for which the position of the lens group to be displaced is displaced to the second position is longer than a time for which the position of the lens group to be displaced is displaced to the first position; and
   a bending portion which can be bent, and which is connected to the front end portion, wherein
   the shape memory element is interpolated into a tube member which can be bent, and the shape memory element and the tube member are extended to the bending portion, and the tube member and the shape memory element are coupled at an end portion of the tube member, toward the bending portion, and the other end of the tube member is fixed to a predetermined part of the front end portion, and the other end of the shape memory element is fixed to the lens group to be displaced.

2. The endoscope according to claim 1, wherein an image-formation range of focusing when a position of the lens group to be displaced is the second position is wider than an image-formation range of focusing when the position of the lens group to be displaced is the first position.

3. The endoscope according to claim 1, wherein the position of the lens group to be displaced is restricted by constraining mechanically between the first position and the second position.

4. The endoscope according to claim 1, wherein a bias spring which exerts a force on the lens group to be displaced, toward the second position is fitted into the drive mechanism which displaces the lens group to be displaced.

* * * * *